United States Patent [19]

Michaelis et al.

[11] 4,367,304

[45] Jan. 4, 1983

[54] NOVEL ORGANIC ANTIMONY-SULFUR COMPOUNDS AND THEIR USE AS STABILIZERS FOR CHLORINE-CONTAINING THERMOPLASTS

[75] Inventors: Klaus-Peter Michaelis, Lindenfels; Wolfgang Wehner, Zwingenberg; Holger Andreas, Bensheim/Auerbach; Horst Müller, Fürth, all of Fed. Rep. of Germany

[73] Assignee: Ciba-Geigy Corporation, Ardsley, N.Y.

[21] Appl. No.: 203,939

[22] Filed: Nov. 4, 1980

[30] Foreign Application Priority Data

Nov. 8, 1979 [CH] Switzerland ............... 10005/79
Jun. 27, 1980 [CH] Switzerland ............... 4963/80

[51] Int. Cl.$^3$ ............... C08K 5/59; C07F 9/90; C07F 9/92
[52] U.S. Cl. ............... 524/204; 260/446; 524/95; 524/96; 524/97; 524/99; 524/102; 524/289; 524/301; 524/327; 524/368; 524/382; 524/392; 524/345; 544/64; 546/4; 524/399; 548/402
[58] Field of Search ............ 260/45.75 B, 446, 346.22; 544/64; 424/296; 528/55, 285; 526/188, 192; 521/89, 121

[56] References Cited

U.S. PATENT DOCUMENTS

| | | | |
|---|---|---|---|
| 1,674,362 | 6/1928 | Hahl | 260/446 |
| 2,226,530 | 12/1940 | Brown et al. | 260/446 |
| 2,510,740 | 6/1950 | Clemence et al. | 260/446 |
| 2,629,724 | 2/1953 | Clemence | 260/446 |
| 2,680,726 | 6/1954 | Weinberg et al. | 260/446 |
| 2,684,956 | 7/1954 | Weinberg et al. | 260/446 |
| 3,035,076 | 5/1962 | Gailliot et al. | 260/446 |
| 3,317,576 | 5/1967 | Malz et al. | 260/446 |
| 3,367,954 | 2/1968 | Leebrick et al. | 260/414 |
| 3,437,716 | 4/1969 | Leebrick | 260/446 |
| 3,504,005 | 3/1970 | Moedritzer et al. | 260/446 |
| 3,887,508 | 6/1975 | Dieckmann | 260/23 XA |
| 4,029,618 | 6/1977 | Dieckmann | 260/23 |
| 4,158,640 | 6/1979 | Dieckmann | 260/45.75 B |
| 4,231,895 | 11/1980 | Dworkin | 260/45.75 B |
| 4,279,807 | 7/1981 | Dworkin | 260/45.75 B |

FOREIGN PATENT DOCUMENTS 515486 11/1952 Belgium .
1531398 7/1968 France .
701965 1/1954 United Kingdom .

OTHER PUBLICATIONS

Chem. Abstracts 81, 72036m (1974).
Heterocyclic Derivatives of Phosphorus, Arsenic, Antimony & Bismuth–Mann, 1970, pp. 625–626.

Primary Examiner—V. P. Hoke
Attorney, Agent, or Firm—Harry Falber

[57] ABSTRACT

Compounds of the formula I, II, III or IV

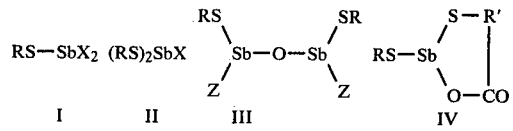

wherein X is halogen, OH, —OR$^1$, —OOCR$^2$, —OOC—R$^4$—COOR$^3$ or —N(R$^5$)(R$^6$), or the two X groups together form a group —O—R$^9$—O— or —OOC—R$^9$—COO—, Y has one of the meanings given for X, or it is —NHR$^5$, —NHNH$_2$ or —NHNH-phenyl, Z has one of the meanings given for X, or is —SR, and R, R$^1$, R$^2$, R$^3$, R$^4$, R$^5$, R$^6$, R$^9$ and R' are organic radicals having the meanings defined hereinbelow, are thermal stabilizers for chlorine-containing thermoplastics particularly for PVC. Their effect can be further intensified by the addition of co-stabilizers.

13 Claims, No Drawings

NOVEL ORGANIC ANTIMONY-SULFUR COMPOUNDS AND THEIR USE AS STABILIZERS FOR CHLORINE-CONTAINING THERMOPLASTS

The invention relates to novel organic antimony-sulfur compounds which can be used as thermal stabilisers for chlorine-containing thermoplastics, particularly for PVC.

The thermal decomposition of chlorine-containing thermoplasts, such as polyvinyl chloride (PVC) constitutes a technically serious problem in the moulding of plastics of this type. A rational processing is virtually possible only by the addition of stabilisers. Additives used for this purpose are especially metal carboxylates, organotin compounds and aminocrotonates. There have been occasionally suggested also antimony mercaptides, for example simple mercaptides of the formula $Sb(SR)_3$ wherein R is alkyl, aryl or arlkyl (U.S. Pat. No. 2,684,956), or ester mercaptides $Sb(SR'COOR'')_3$ wherein R' is alkylene, arylene or aralkylene and R'' is substituted or unsubstituted alkyl, aryl or arylalkyl (U.S. Pat. No. 2,680,726). A representative of the latter type is the compound $Sb(SCH_2COO\text{-}isoC_8H_{17})_3$, known under the tradename "Irgastab 511". The disadvantage of antimony mercaptides of this kind is that their stability to storage and to light is lower than that or organotin compounds. There existed therefore a commercial interest in antimony stabilisers having a higher stability to storage and to the action of light.

It has now been found that, compared with the known tris-mercaptides, specific antimony mercaptides of which the Sb atom is bound only to 1 or 2 mercapto groups have an increased storage stability and an improved light stability, and in their action as PVC stabilisers they are equal or superior to the known tris-mercaptides. Furthermore, compared with these tris-mercaptides they are distinguished also by the fact that when added to chlorine-containing polymers, the thermoplastic processing of these polymers is facilitated. The said specific antimony mercaptides are novel compounds.

The present invention relates therefore to the compounds of the formula I, II, III or IV

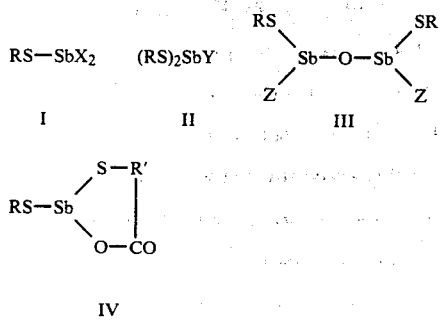

wherein
X is Cl, Br, I, OH, $-OR^1$, $-OOCR^2$, $-OOC-R^4-COOR^3$ or $-N(R^5)(R^6)$, or the two X groups together form a group $-O-R^9-O-$ or $-O-CO-R^9-COO-$,
Y has one of the meanings given for X, or it is $-NHR^5$, $-NHNH_2$ or $-NHNH$-phenyl,
Z has one of the meanings given for X, or it is SR,
R is $C_1-C_6$-alkyl substituted by one or two of the groups $-OH$, $-OCOR^7$, $-OR^8$, $-SR^8$ or $-COOR^8$,
R' is $-CH_2-$ or $-CH_2CH_2-$, and
$R^1$ is $C_1-C_{18}$-alkyl, $C_1-C_6$-alkyl substituted by $-OR_8$, $-SR_8$ or $-OCOR^7$, or $R^1$ is $C_6-C_{10}$-aryl, $C_7-C_9$-phenylalkyl or $C_5-C_8$-cycloalkyl, $R^2$ is $C_1-C_{18}$-alkyl, $C_2-C_{18}$-alkenyl, $C_5-C_8$-cycloalkyl, $C_6-C_{10}$-aryl, or phenyl or $C_7-C_9$-phenylalkyl each substituted by $C_1-C_4$-alkyl, hydroxyl and/or halogen, $R^3$ is $C_1-C_{12}$-alkyl, allyl, cyclohexyl or phenyl, $R^4$ is $C_2-C_{12}$-alkylene, $C_2-C_6$-alkenylene, $C_5-C_{12}$-cycloalkylene or cycloalkenylene, phenylene or halophenylene, $R^5$ and $R^6$ can be identical or different and are each $C_1-C_{12}$-alkyl, benzyl or cyclohexyl, or $R^5$ and $R^6$ together with the N atom form a pyrrolidine, piperidine or morpholine group, $R^7$ is $C_1-C_{18}$-alkyl, $CH_3COCH_2-$, cyclohexyl, benzyl, $C_6-C_{10}$-aryl, or phenyl or $C_7-C_9$-phenylalkyl each substituted by $C_1-C_4$-alkyl, hydroxyl and/or halogen, $R^8$ is $C_1-C_{18}$-alkyl, allyl, cyclohexyl or phenyl, and $R^9$ is $C_2-C_6$-alkylene, $C_3-C_6$-alkylene interrupted by O, S or $(R^5)N$, or it is propylene substituted by $-OR^8$ or $-OCOR^7$; and to the use of these compounds as stabilisers for chlorine-containing thermoplastics.

The group R is a mono- or disubstituted alkyl group. In the case of a disubstituted alkyl group, the substituents can be identical or different. The alkyl group itself can be straight-chain or branched-chain. Examples of the group R are: 2-hydroxyethyl, 2-hydroxypropyl, 2,3-dihydroxypropyl, 2-hydroxybutyl, 2-hydroxy-3-butoxypropyl, 2-octyloxyethyl, 2-phenoxypropyl, 2-acetoxybutyl, 2-(dodecylmercapto)-ethyl, 2-hydroxy-3-isopropoxypropyl, 2-hydroxy-3-caproyloxypropyl, 2-lauroyloxyethyl, 2,3-dibutyroylpropyl, 2,3-bis-[4-hydroxy-3,5-di-t-butyl-benzoyloxy]-propyl, 2,3-bis-[2-(4-hydroxy-3,5-di-t-butyl-phenyl)-propionyloxy]-propyl, 2-benzoyloxybutyl, 2,3-bis-(acetoacetoxy)-propyl or 2-acetoxy-3-phenoxypropyl. R is preferably a lower alkyl group substituted by one or two of the groups $-COOR^8$, for example octyloxycarbonylmethyl, dodecyloxycarbonylmethyl, 2-(decylooxycarbonyl)-ethyl, 2-(butyloxycarbonyl)-propyl, 1,3-bis-(octadecyloxycarbonyl)-2-propyl or 2,3-bis-(2-ethylhexyloxycarbonyl)-propyl. Particularly preferably, R is a group $-CH_2COOR^8$, wherein $R^8$ is a $C_8-C_{14}$-alkyl group.

When $R^1$, $R^2$, $R^3$, $R^5$, $R^6$, $R^7$ or $R^8$ is alkyl, this can be a straight-chain or branched-chain alkyl group, for example methyl, ethyl, isopropyl, tert-butyl, sec-amyl, n-hexyl, 2-ethylhexyl, n-decyl or n-dodecyl. As alkyl, $R^1$, $R^2$, $R^7$ and $R^8$ can in addition be longer-chain alkyl, such as tetradecyl, hexadecyl or octadecyl, and are preferably $C_8-C_{14}$-alkyl.

As alkyl substituted by $-OR^8$, $-SR^8$ or $-OCOR^7$, $R^1$ can be for example: 2-butoxyethyl, 3-octyloxypropyl, 2-isopropoxypropyl, 2-(dodecylmercapto)-ethyl, 2-(tert-butylmercapto)-propyl, 2-acetoxyethyl, 2-lauroyloxypropyl or 3-stearoyloxyethyl.

$R^1$ or $R^2$ as cycloalkyl can be for example: cyclopentyl, cyclohexyl or cyclooctyl. As alkenyl, $R^2$ can be for example: vinyl, propenyl, pentadienyl, hexenyl, decenyl or heptadecenyl.

$R^1$, $R^2$ or $R^7$ as aryl can be phenyl or naphthyl; $R^2$ and $R^7$ can also be phenyl substituted by lower-alkyl, hydroxyl and/or halogen, for example: 4-tolyl, 2-tolyl, 4-tert-butylphenyl, 3-chlorophenyl, 2,4-dichlorophenyl, 4-ethyl-2-chlorophenyl, 3-hydroxyphenyl, 4-chloro-2- hydroxyphenyl, 2-methyl-4-hydroxyphenyl or 3,5-di-t-butyl-4-hydroxyphenyl.

As phenylalkyl, $R^1$ can be for example: benzyl, 2-phenylethyl, 1-phenylethyl or 2-phenylpropyl, $R^2$ and $R^7$ as phenylalkyl substituted by lower alkyl, hydroxyl and/or halogen can be for example: 4-butylbenzyl, 3-chlorobenzyl, 2-methyl-4-hydroxybenzyl or 2-(3,5-di-t-butyl-4-hydroxyphenyl)-ethyl.

$R^4$ is a bivalent radical of a dicarboxylic acid, and it can be for example: 1,2-ethylene, 1,2-propylene, 1,3-propylene, 1,4-butylene, 1,2-octylene, 1,2-vinylene, 1-propen-2,3-diyl, cyclopentan-1,2-diyl, cyclohexan-1,2-diyl, cyclooctan-1,2-diyl, 1-cyclohexan-4,5-diyl, 2-norbornen-5,6-diyl, 1,2-phenylene or 4-chloro-1,2-phenylene.

$R^9$ is the bivalent radical of a diol or of a dicarboxylic acid, and can be for example: 1,2-ethylene, 1,2-propylene, 1,3-propylene, 1,2-butylene, 1,4-butylene, 2,2-dimethyl-1,3-propylene, 3-oxa-1,3-propylene, 3-oxa-1,5-pentylene, 3-methylaza-1,5-pentylene, 3-phenylaza-1,5-penthylene, 3-octyloxy-1,2-propylene, 3-dodecyloxy-1,2-propylene, 2-stearoxyloxy-1,3-propylene, 3-phenyloxyl, 2-propylene, 3-lauroyloxy-1,2-propylene, 3-steearyloxy-1,2-propylene, 3-acetoacetyloxy-1,2-propylene or 2-stearoyloxy-1,3-propylene.

Preferred compounds of the formula I, II or III are those wherein X, Y or Z is chlorine. Also preferred are compounds of the formula I or II wherein X or Y is one of the groups $-OR^1$, $-OOC-R^4-COOR^3$ or $-OOCR^2$.

Examples of compounds of the formula I are the compounds of the following formulae:

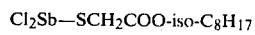
Cl₂Sb—SCH₂COO-iso-C₈H₁₇

Cl₂Sb—SCH₂CH₂COOC₄H₉

Cl₂Sb—SCH₂CH₂OH

Cl₂Sb—SCH₂CH₂OOC—C₁₁H₂₃

Cl₂Sb—SCH₂CH(OH)CH₂OOC—C₁₇H₃₅

(HO)₂Sb—SCH₂CH₂OC₆H₅

(C₄H₉O)₂Sb—SCH₂COOC₁₂H₂₅

(C₁₂H₂₅O)₂Sb—SCH₂CH₂COOC₁₂H₂₅

(C₄H₉OCH₂CH₂O)₂Sb—SCH₂CH₂OOC—C₁₁H₂₃

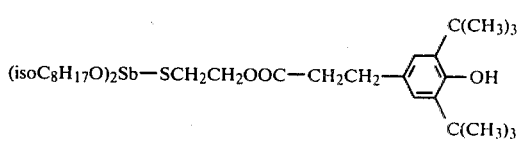

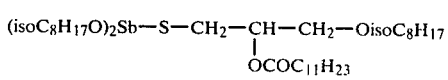

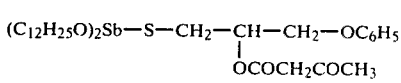

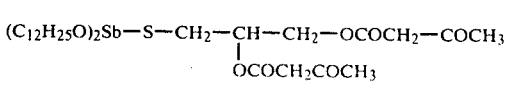

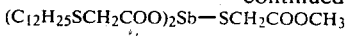
(C₁₂H₂₅SCH₂COO)₂Sb—SCH₂COOCH₃

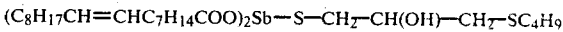
(C₈H₁₇CH=CHC₇H₁₄COO)₂Sb—S—CH₂—CH(OH)—CH₂—SC₄H₉

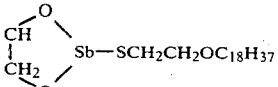

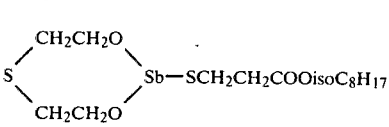

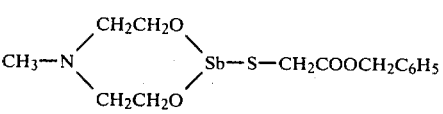

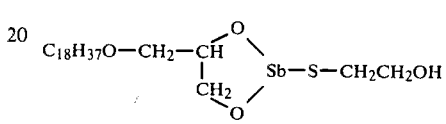

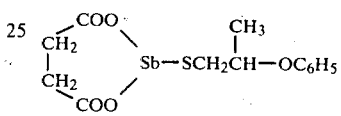

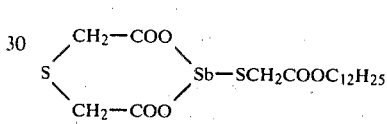

Examples of compounds of the formula II are:

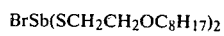
BrSb(SCH₂CH₂OC₈H₁₇)₂

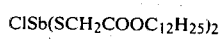
ClSb(SCH₂COOC₁₂H₂₅)₂

ClSb(SCH₂CH(OH)CH₂O—sec-C₄H₉)₂

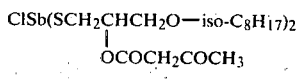
ClSb(SCH₂CHCH₂O—iso-C₈H₁₇)₂
    |
    OCOCH₂COCH₃

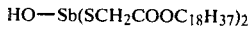
HO—Sb(SCH₂COOC₁₈H₃₇)₂

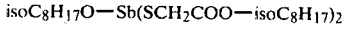
isoC₈H₁₇O—Sb(SCH₂COO—isoC₈H₁₇)₂

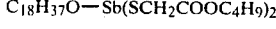
C₁₈H₃₇O—Sb(SCH₂COOC₄H₉)₂

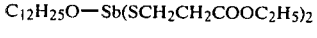
C₁₂H₂₅O—Sb(SCH₂CH₂COOC₂H₅)₂

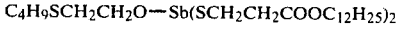
C₄H₉SCH₂CH₂O—Sb(SCH₂CH₂COOC₁₂H₂₅)₂

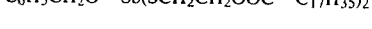
C₆H₅CH₂O—Sb(SCH₂CH₂OOC—C₁₇H₃₅)₂

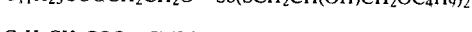
C₁₁H₂₃COOCH₂CH₂O—Sb(SCH₂CH(OH)CH₂OC₄H₉)₂

C₆H₅CH₂COO—Sb(SCH₂COOisoC₈H₁₇)₂

C₁₈H₃₇COO—Sb(SCH₂COOCH₃)₂

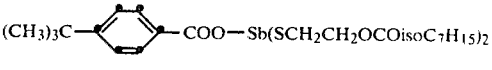

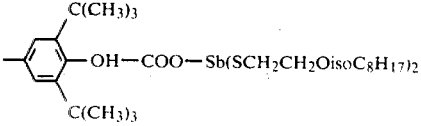

-continued

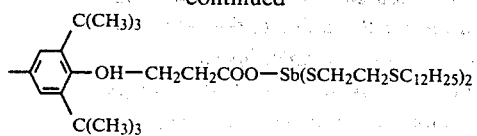

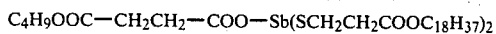

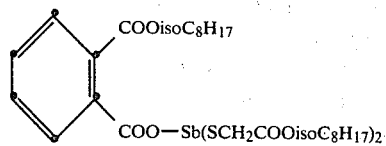

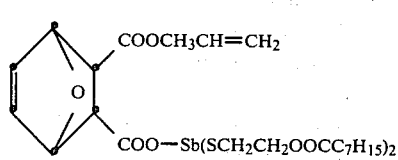

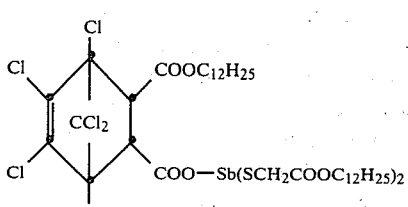

(C$_4$H$_9$)$_2$N—Sb(SCH$_2$CH$_2$COOC$_4$H$_9$)$_2$

C$_6$H$_{11}$NH—Sb(SCH$_2$CH$_2$O—iso-C$_8$H$_{17}$)$_2$

C$_6$H$_5$NHNH—Sb(SCH$_2$CHCH$_2$OC$_{12}$H$_{25}$)$_2$

Examples of compounds of the formula III are:

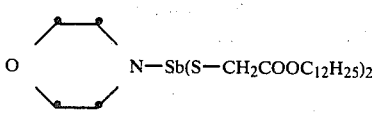

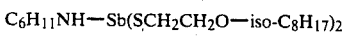

(C$_{12}$H$_{25}$OOCCH$_2$S)$_2$Sb—O—Sb(SCH$_2$COOC$_{12}$H$_{25}$)$_2$

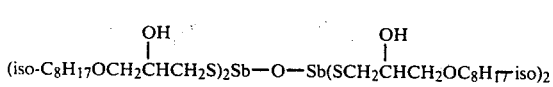

Examples of compounds of the formula IV are:

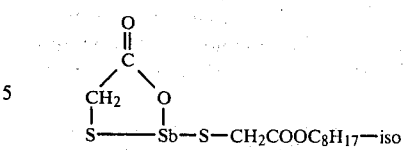

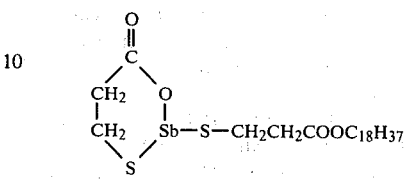

Compounds of the formulae I and II can be produced in many cases by comproportionation of antimony tris-mercaptides with compound SbX$_3$ or SbY$_3$:

Sb(SR)$_3$ + 2 SbX$_3$ → 3 RS—SbX$_2$     (I)

2Sb(SR)$_3$ + SbX$_3$ → 3(RS)$_2$SbY     (II)

Compounds SbX$_3$ and SbY$_3$ suitable for this purpose are in particular the antimony halides SbCl$_3$, SbBr$_3$, SbJ$_3$, antimony alcoholates, for example Sb(OC$_2$H$_5$)$_3$ or Sb(OC$_6$H$_{13}$)$_3$, and antimony carboxylates, for example Sb(OOCCH$_3$)$_3$.

These comproportionation reactions can be performed without or in an inert solvent. The necessary temperatures are between 100° and 200° C. Suitable solvents are for example toluene, xylene or tetrahydrofuran. The trismercaptides Sb(SR$_3$ are known compounds, as are described for example in the U.S. Pat. Nos. 2,684,956 and 2,680,726 mentioned hereinbefore.

The compounds of the formulae I and II in which X and Y are halogen are usable as intermediates for the other compounds of the formulae I and II. Particularly suitable for this purpose are the corresponding chlorine compounds V and VI:

RS—SbCl$_2$     (V)

(RS)$_2$SbCl     (VI)

There are thus formed from V and Vi by reaction with R$^1$OH—in the presence or absence of HCl acceptors—compounds of the formulae I and II wherein X or Y is R$^1$O—. Compounds of the formula I or II wherein X or Y is R$^2$COO— or R$^3$OOC—R$^4$—COO— are formed from the chlorine compounds V or VI by reaction with monocarboxylic acids or with dicarboxylic acid half-esters, either in the presence of equivalent amounts of a base (preferably of a tertiary amine), or by reaction with the alkali metal salts of such acids.

By hydrolysis of compounds of the formula V are obtained compounds of the formula I wherein X is OH, and compounds of the formula III wherein Z is OH. By hydrolysis of compounds of the formula VI are obtained compounds of the formula II wherein Y is OH, and compounds of the formula III wherein Z is SR.

The compounds of the formula I or II wherein X and Y are each a group (R$^5$) (R$^6$)N— can be produced from the chlorine compounds V or VI by reaction with secondary amines, whereby the HCl acceptor used can be either this amine in excess or another base in an equivalent amount.

There are obtained in an analogous manner from compounds of the formula VI, by reaction with primary amines, hydrazine or phenylhydrazine, the compounds of the formula II wherein Y is —NHR$^5$, —NHNH$_2$ or —NHNH-phenyl.

The compounds of the formula I wherein both X groups together form —O—R$^9$—O— can be produced from the compounds V by reaction with one equivalent of a compound HO—R$^9$—OH in the presence of 2 equivalents of an HCl acceptor. Compounds of the formula I wherein both X groups together form —O—CO—R$^9$—CO—O— can be produced from the compounds V by reaction with an alkali metal salt of a dicarboxylic acid of the formula HOOC—R$^9$—COOH.

The compounds of the formula IV can be produced from compounds of the formula VII

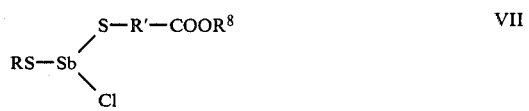

by alkaline hydrolysis, the meaning of R$^8$ being as defined hereinbefore.

The compounds of the formulae V and VI can be produced also be reaction of antimony trichloride with the corresponding mercapto compounds RSH:

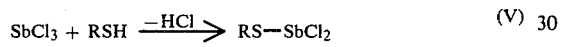

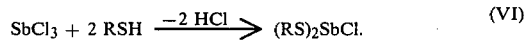

These reactions are preferably performed in an organic solvent, for example in methylene chloride. Suitable as HCl acceptors are organic or inorganic bases, particularly alkali carbonates, such as NaHCO$_3$ or K$_2$CO$_3$, in solid form.

Also mixtures of compounds can be formed with the methods of synthesis described herein. For example in the production of a compound of the formula V by means of comproportionation, a certain amount of VI can occur as a by-product. Or in the case of hydrolysis of compounds of the formula V, there can be formed besides products of the formula I also products of the formula III. For most purposes, mixtures of this kind can be used in the same manner as the pure compounds. When however the pure compounds are desired, they can be obtained by the customary purification methods, such as fractional distillation, crystallisation or chromatography.

The antimony mercaptides of the formulae I, II, III and IV can be used as stabilisers for chlorine-containing thermoplastic, for example for polymers and copolymers of vinyl chloride or vinylidene chloride, chlorinated polyolefins, post-chlorinated polyvinyl chloride, or chlorinated rubber. The stabilisation of polyvinyl chloride (PVC) is of particular importance. The materials concerned can be suspension PVC, emulsion PVC or polymers produced by bulk polymerisation.

The compounds of the formulae I, II, III and IV are added to the chlorine-containing thermoplastics in an amount of 0.1 to 5 percent by weight, relative to the thermoplastics. The amount preferably used is 0.5 to 3 percent by weight. It is also possible to use mixtures of two or more compounds of the formulae I, II, III and IV.

Also precursors of the stabilisers according to the invention can be added to the thermoplastics. It is possible to add for example, instead of a compound of the formula I, a mixture of Sb (SR)$_3$ and Sb X$_3$ (preferably in the molar ratio of 1:2), from which under the conditions of thermoplastic moulding the compound of the formula I can form in the thermoplastics. The direct addition of the compounds of the formulae I, II, III and IV is however preferred.

The incorporation of the stabilisers into the polymeric substrates can be effected by the customary processes for incorporating additives into thermoplastics, for example by a mixing together of the constituents in powder form and subsequent moulding, or by addition of the stabilisers on a roll mill or in a kneading machine. There can be incorporated simultaneously other additives commonly known in the technology of chlorine-containing thermoplastics, for example lubricants, plasticisers, fillers, additives for increasing impact strength, pigments, light stabilisers and antioxidants, or further thermostabilisers, for example metal carboxylates or organic phosphites.

Of particular importance is the addition of co-stabilisers, especially co-stabilisers from the series of pyrocatechol derivatives. It is known, for example from the U.S. Pat. Nos. 4,029,618 and 4,158,640, that pyrocatechol and derivatives thereof have a synergistic effect together with organic antimony compounds as stabilisers for chlorine-containing thermoplastics. Co-stabilisers of this type which synergistically intensify the action of the basic stabiliser are also called boosters. This type of booster effect of pyrocatechol and of derivatives of pyrocatechol is to be observed also when they are used in combination with the compounds of the formulae I, II, III and IV. Examples of synergistically acting pyrocatechols of this kind are the compounds of the following formulae:

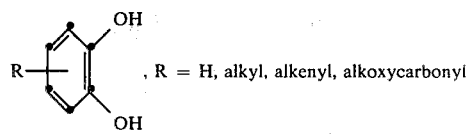

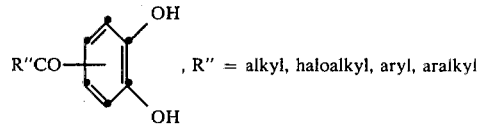

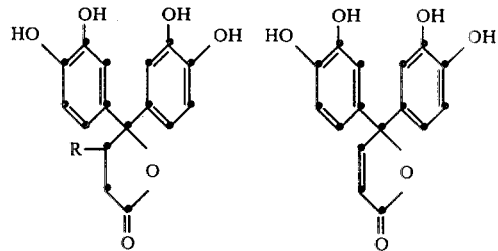

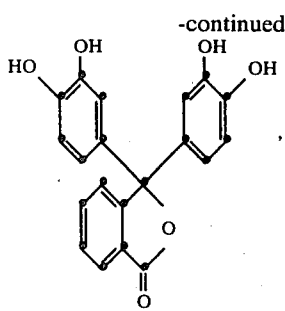

as well as antimony phenolates and tin phenolates of such pyrocatechols, for example the following compounds:

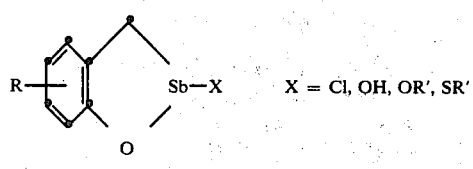

$X'$ = alkylene, oxaalkylene, thioalkylene, phenylene

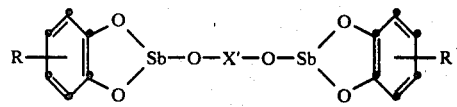

$R'$ = alkyl, aryl, aralkyl

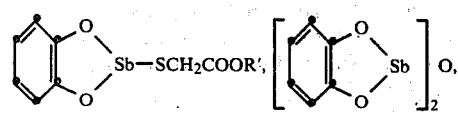

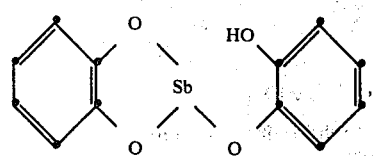

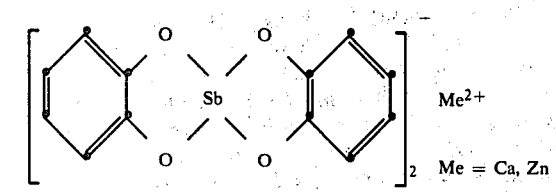

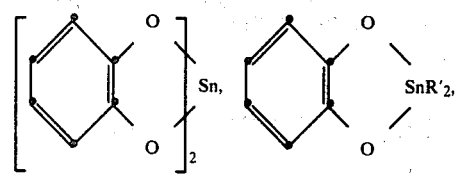

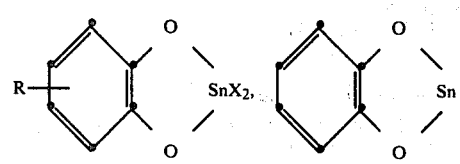

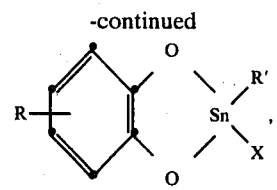

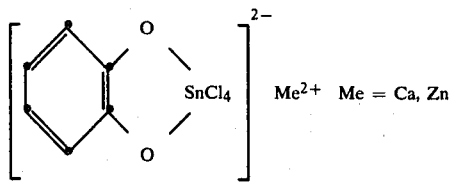

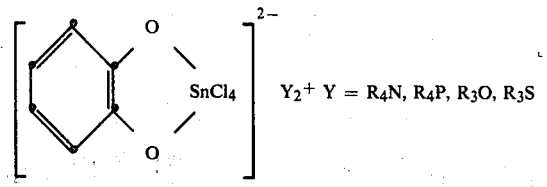

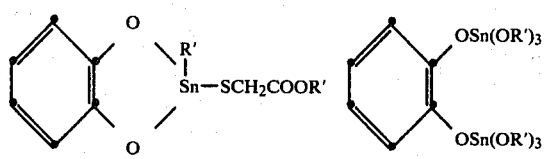

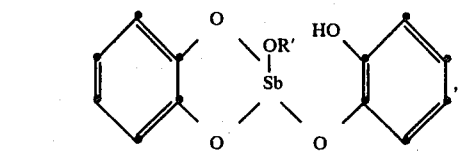

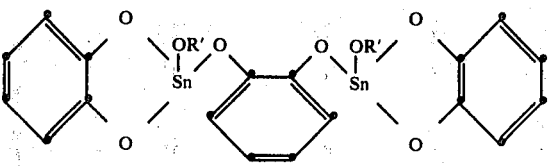

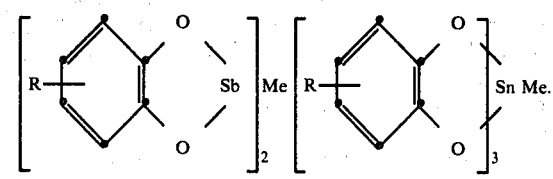

Further synergistic pyrocatechol derivatives are the cyclic borates or phosphites of pyrocatechols, such as the compounds of the type:

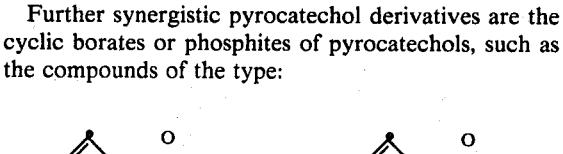

wherein R and X have the meanings defined in the foregoing.

Other synergistic pyrocatechol derivatives are the halogenated pyrocatechols, for example: 3-chloro-, 3,4- dibromo-, 3-bromo-4-tert-butyl- or 3,4,5,6-tetrabromopyrocatechol.

These co-stabilisers are used in an amount of 2–50 percent by weight, relative to the amount of employed compound I, II, III or IV, so that the weight ratio of stabiliser:co-stabiliser is 2:1 to 98:2. The optimum quantity ratio has to be experimentally ascertained for each stabiliser/co-stabiliser combination.

The stabilised chlorine-containing thermoplastics according to the invention can be moulded into shape by the methods customarily used therefor, for example by means of extrusion, injection moulding or calendering, or by being processed as plastisols.

The following Examples further illustrate production and use of the compounds of the formulae I, II, III and IV. Parts are by weight and temperatures are degrees Centigrade.

EXAMPLE 1

Comproportionation of SbCl$_3$ in solution 114.2 g; (0.5 mol) of antimony trichloride with 731 g (1 mol) of antimony tris-thioglycolic acid isooctyl ester in 200 ml of toluene are refluxed for 20 hours. After cooling, the slight amount of impurities is separated by filtration, and the solvent is removed in vacuo. There is obtained in practically quantitative yield a colourless viscous oil having the elements in the ratio Sb:S:Cl=1:1.924:0.996, with an H-NMR signal for the thiomethylene protons at $\delta=3.90$ ppm.

That corresponds to the compound of the formula

ClSb(SCH$_2$COO-isoC$_8$H$_{17}$)$_2$ (compound No. 1).

The same result is obtained by carrying out the test in ethylene chloride instead of in toluene.

In an analogous manner are obtained, from 228.2 g (1 mol) of SbCl$_3$ and 365.4 g (0.5 mol) of Sb(SCH$_2$COO-isoC$_8$H$_{17}$)$_3$, the compound No. 2

Cl$_2$SbSCH$_2$COO-isoC$_8$H$_{17}$ in the form of a crystalline solid, which melts at 48°–49°. The element ratio according to analysis is 1:0.92:2.1; and the H-NMR spectrum shows a singlet for the thiomethylene protons at $\delta=4.17$.

EXAMPLE 2

Comproportionation of SbCl$_3$ without solvent 45.6 g of antimony trichloride and 78 g of Sb[SCH$_2$CH(OH)CH$_2$O-iso-C$_8$H$_{17}$]$_3$ are shaken for 12 hours at room temperature. The initially undissolved SbCl$_3$ disappears during this time. The resulting slightly yellowish oil is crude monomercaptide

Cl$_2$SbSCH$_2$CH(OH)CH$_2$O-isoC$_8$H$_{17}$ (compound No. 3).

There is obtained in an analogous manner, from 11.4 g of SbCl$_3$ and 78 g of the above tris-mercaptide, the compound No. 4:

ClSb[SCH$_2$CH(OH)CH$_2$O-isoC$_8$H$_{17}$]$_2$ as a light-yellow liquid.

EXAMPLE 3

Alcoholysis of antimony chloromercaptides 113 g of ClSb(SCH$_2$COO-isoC$_8$H$_{17}$)$_2$ (compound No. 1) are dissolved in 200 ml of diethyl ether. A solution of 26 g of 2-ethylhexanol and 20 g of triethylamine in 100 ml of diethyl ether is slowly added dropwise with stirring, and the mixture is subsequently refluxed for 1 hour. After cooling, the amine hydrochloride which has precipitated is filtered off, and the solution is concentrated by evaporation. The yield is 121 g of a product of the formula

isoC$_8$H$_{17}$OSb(SCH$_2$COO-isoC$_8$H$_{17}$)$_2$ (compound No. 5) as a transparent oily liquid, of which the H-NMR spectrum is in agreement with the above formula.

Elementary analysis: Found: Sb 18.3%; S 9.6%. Calculated: Sb 18.5%; S 9.9%.

There are obtained in an analogous manner, from 113 g of ClSb(SCH$_2$COO-isoC$_8$H$_{17}$)$_2$, 54 g of octadecanol (stearyl alcohol) and 20 g of triethylamine, 133 g of the compound No. 6:

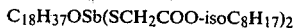
C$_{18}$H$_{37}$OSb(SCH$_2$COO-isoC$_8$H$_{17}$)$_2$ as a colourless wax, which melts at 48°–49°.

Analysis: Found: Sb 15.5%; S 8.3%. Calculated: Sb 15.9%; S 8.4%.

There are obtained in an analogous manner, from 99 g of Cl$_2$Sb SCH$_2$COO-isoC$_8$H$_{17}$ (compound No. 2), 135 g of octadecanol and 51 g of triethylamine, 215 g of the compound No. 7:

(C$_{18}$H$_{37}$O)$_2$SbSCH$_2$COO-isoC$_8$H$_{17}$ as colourless wax, which melts at 53°–54°.

Analysis: Found: Sb 12.6%; S 6.6%. Calculated: Sb 13.0%; S 6.9%.

EXAMPLE 4

Reaction of antimony chloromercaptides with carboxylic acids 11.2 g of ClSb(SCH$_2$COO-isoC$_8$H$_{17}$)$_2$ are dissolved in 20 ml of diethyl ether. There is simultaneously added dropwise, with stirring, a solution of 2 g of triethylamine in 10 ml of ether, and 4.8 g of endomethylenetetrahydrophthalic acid monobutyl ester in 20 ml of ether, and the whole is refluxed for 1 hour. The amine hydrochloride which has precipitated is filtered off, and the filtrate is concentrated by evaporation. The yield is 13.6 g of a product of the formula (compound No. 8)

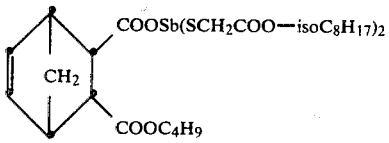

in the form of colourless wax.

Elementary analysis: Found: Sb 15.8%; S 8.2%. Calculated: Sb 16.1%; S 8.5%.

In an analogous manner are obtained:

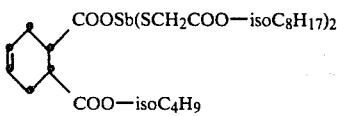

(compound No. 9) yellowish oil;

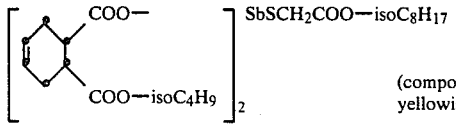

(compound No. 10) yellowish oil;

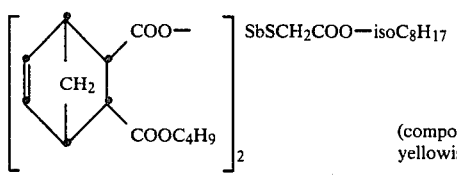

(compound No. 11) yellowish oil;

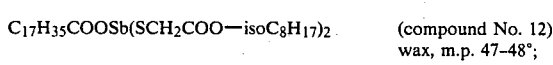

(compound No. 12) wax, m.p. 47-48°;

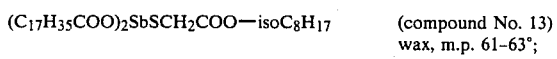

(compound No. 13) wax, m.p. 61-63°;

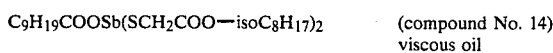

(compound No. 14) viscous oil from "Versatic acid 10", a commercial mixture of branched-chain $C_{10}$-monocarboxylic acids.

EXAMPLE 5

Reaction of $SbCl_3$ with thioglycolic esters 4.56 g of $SbCl_3$, 4.08 g of $HSCH_2COO$-$isoC_8H_{17}$ and 1.85 g of $NaHCO_3$ in 50 ml of methylene chloride are reacted reflux temperature. After the evolution of gas has finished, the reaction mixture is filtered, and the filtrate is concentrated in vacuo. There remains a colourless oil consisting mainly of the compound No. 2. The NMR spectrum of the crude product shows the presence of the compound $C_8H_{17}OOCCH_2S$—Sb(Cl)—O—Sb(Cl)—$SCH_2COOC_8H_{17}$ as by-product in an amount of about 10 mol %.

There is obtained in an analogous manner, from 4.56 g of $SbCl_3$, 8.16 g of thioglycolic acid iso-octyl ester and 3.69 g of $NaHCO_3$, a crude product in the form of a colourless oil consisting mainly of the compound No. 1, and as by-product about 10 mol % of the compound $(C_8H_{17}OOCCH_2S)_2Sb$—O—Sb$(SCH_2COOC_8H_{27})_2$.

EXAMPLE 6

Stabilisation of PVC

The following recipe suitable for producing drinking-water tubes was used:

| | |
|---|---|
| suspension PVC of K value 68 | 100 parts |
| chalk | 1.0 part |
| TiO$_2$ (Rutil) | 1.0 part |
| paraffin wax | 0.8 part |
| calcium stearate | 0.8 part |
| stabiliser | 0.4 part |
| | 104 parts |

The constituents were mixed dry, and the mixture was subjected on a laboratory roll mill at 200° to a long-duration roll test. The discoloration occurring was ascertained, after 3, 6 and 12 minutes respectively, by determination of the Yellowness Index on specimens taken from the 0.3 mm thick rolled sheet. To provide a comparison with the prior art, there was used "Irgastab 511", an antimony tris-mercapto ester of the formula $Sb(CH_2COO$-$isoC_8H_{17})_3$. The results are summarised in the following Table.

| Employed stabiliser | Yellowness-Index after | | |
|---|---|---|---|
| | 3 min. | 6 min. | 12 min. |
| Irgastab 511 (comparison) | 20.8 | 24.2 | brown |
| compound No. 1 | 12.1 | 19.3 | brown |
| compound No. 2 | 11.8 | 22.1 | brown |
| compound No. 1 + 4-tert-butyl-pyrocatechol in the ratio of 19:1 | 7.9 | 16.4 | brown |

EXAMPLE 7

Stabilisation of PVC with the addition of a co-stabiliser

A mixture was prepared as in Example 6 except that there was used, instead of 0.4 part of stabiliser, 0.35 part of stabiliser and 0.05 part of tetrabromopyrocatechol as the co-stabiliser.

| Stabiliser | Yellowness Index after | | |
|---|---|---|---|
| | 3 min. | 6 min. | 12 min. |
| compound No. 6 | 7.8 | 11.2 | brown |
| No. 7 | 8.5 | 21.4 | brown |
| No. 12 | 7.4 | 11.2 | brown |
| No. 13 | 7.7 | 11.7 | brown |
| No. 14 | 6.6 | 9.5 | brown |

What is claimed is:
1. A compound of the formula I, II or III

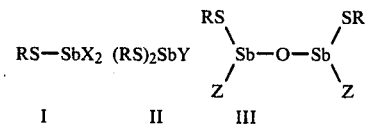

wherein

X is Cl, Br, I, OH, —OR$^1$, —OOCR$^2$, OOC—R$^4$—COOR$^3$, or the two X groups together form a group —O—R$^9$—O— or —OCO—R$^9$—COO—, Y has one of the meanings given for X, or it is —NHR$^5$, —NHNH$^2$ or —NHNH-phenyl, Z has one of the meanings given for X, or it is SR, R is $C_1$-$C_6$-alkyl substituted by one or two of the groups —OCOR$^7$, —OR$^8$, —SR$^8$ or —COOR$^8$, R$^1$ is $C_1$-$C_{18}$-alkyl, $C_1$-$C_6$-alkyl substituted by —OR$_8$, —SR$^8$ or —OCOR$^7$, or R$^1$ is $C_6$-$C_{10}$-aryl, $C_7$-$C_9$-phenylalkyl or $C_5$-$C_8$-cycloalkyl, R$^2$ is $C_1$-$C_{18}$-alkyl, $C_2$-$C_{18}$-alkenyl, $C_5$-$C_8$-cycloalkyl, $C_6$-$C_{10}$-aryl, or phenyl or $C_7$-$C_9$-phenylalkyl each substituted by $C_1$-$C_4$-alkyl, hydroxyl or halogen, R$^3$ is $C_1$-$C_{12}$-alkyl, allyl, cyclohexyl or phenyl, R$^4$ is $C_2$-$C_{12}$-alkylene, $C_2$-$C_6$-alkenylene, $C_5$-$C_{12}$-cycloalkylene or cycloalkenylene, phenylene or halophenylene, R$^5$ is $C_1$ to $C_{12}$ alkyl, benzyl or cyclohexyl;

R$^7$ is $C_1$-$C_{18}$-alkyl, $CH_3COCH_2$—, cyclohexyl, benzyl, $C_6$-$C_{10}$-aryl, or phenyl or $C_7$-$C_9$-phenylalkyl each substituted by $C_1$-$C_4$-alkyl, hydroxyl or halogen, R$^8$ is $C_1$-$C_{18}$-alkyl, allyl, cyclohexyl or phenyl, and $R^9$ is $C_2$–$C_6$-alkylene, $C_3$–$C_6$-alkylene interrupted by O, S or $(R^5)$N, or it is propylene substituted by —$OR^8$ or —$OCOR^7$.

2. A compound of the formula I, II or III according to claim 1, wherein X, Y or Z is chlorine.

3. A compound of the formula I or II according to claim 1, wherein X or Y is any one of the groups —$OR^1$, —OOC—$R^4$—$COOR^3$ or —$OOCR^2$.

4. A compound according to claim 1, wherein R is a $C_1$–$C_6$-alkyl group substituted by one or two groups —$COOR^8$.

5. A compound according to claim 4, wherein R is a group —$CH_2COOR^8$, and $R^8$ is a $C_8$–$C_{14}$-alkyl group.

6. A chlorine-containing thermoplastic material stabilised by an antimony mercaptide, which thermoplastic contains 0.1 to 5 percent by weight of a compound of claim 1 as stabiliser.

7. A stabilised thermoplastic material according to claim 6, which thermoplastic is polyvinyl chloride.

8. A stabilized thermoplastic material according to claim 6, which thermoplastic contains o-dihydric phenols or the antimony, tin, phosphorus or boron derivatives thereof as a co-stabilizer.

9. A stabilised thermoplast according to claim 8, wherein the weight ratio of stabiliser to co-stabiliser is 2:1 to 98:2.

10. A stabilised thermoplastic material according to claim 6, which thermoplastic contains a calcium or zinc carboxylate as a co-stabiliser.

11. A method of stabilizing chlorine-containing thermoplastic materials against the adverse effects of heat and light which comprises incorporating into said material an effective stabilizing amount of a compound according to claim 1.

12. The method of claim 11, wherein said chlorine-containing thermoplastic material is polyvinyl chloride.

13. The method of claim 11, wherein a co-stabilizer selected from the group consisting of o-dihydric phenols and the antimony, tin, phosphorus and boron derivatives thereof is additionally incorporated.

* * * * *